| United States Patent [19] | [11] Patent Number: 4,923,811 |
| Simon et al. | [45] Date of Patent: May 8, 1990 |

[54] CARRYING OUT ENZYMATIC OXIDATIONS

[75] Inventors: Helmut Simon, Freising; Helmut Guenther, Haag, both of Fed. Rep. of Germany

[73] Assignee: BASF Aktiengesellschaft, Ludwigshafen, Fed. Rep. of Germany

[21] Appl. No.: 90,444

[22] Filed: Aug. 28, 1987

[30] Foreign Application Priority Data

Sep. 13, 1986 [DE] Fed. Rep. of Germany ....... 3631228

[51] Int. Cl.$^5$ .......................... C12P 7/40; C12P 7/44; C12P 7/62; C07P 41/00
[52] U.S. Cl. .................................. 435/136; 435/135; 435/142; 435/143; 435/191; 435/250
[58] Field of Search ............... 435/136, 135, 142, 143, 435/280, 190

[56] References Cited

FOREIGN PATENT DOCUMENTS 0099157 1/1984 European Pat. Off. .
0119088 9/1979 Japan ................................... 435/136

OTHER PUBLICATIONS

Angew. Chem. 97 (1985), 541.

Primary Examiner—Herbert J. Lilling
Attorney, Agent, or Firm—Keil & Weinkauf

[57] ABSTRACT

A process for carrying out enzymatic oxidations is described.

1 Claim, No Drawings

CARRYING OUT ENZYMATIC OXIDATIONS

The present invention relates to a process for carrying out enzymatic oxidations.

It is known that 2-oxocarboxylic acids can be reduced with the aid of microorganisms to which the reduction equivalents are made available via an electron carrier which is regenerated electrochemically (European Laid-Open Application 99,157 and Angew. Chem. 97 (1985), 541). In particular, methyl viologen or benzyl viologen is used as the electron carrier. It has not been possible to date to reverse the reduction of -oxo acids, even when the reduced viologen which may be formed in a small amount is quantitatively reoxidized with a strongly electropositive oxidizing agent, such as potassium hexacyanoferrate (S. Neumann, Thesis, Munich Technical University, 1985).

We have found that oxidation reactions can be carried out with certain viologens.

The present invention relates to a process for carrying out enzymatic oxidations by transferring electrons from the substrate to be oxidized to an electron acceptor in the presence of a redox enzyme, wherein the electrons are transferred from the redox enzyme to the electron acceptor with the aid of CAV or CYV.

CAV is the viologen 1,1'-dicarbamoylmethyl-4,4'-dipyridinium dication and CYV is the viologen 1,1'-dicyanomethyl-4,4'-dipyridinium dication (cf. Chem. Soc. Rev. 10 (1981), 49–82).

Reduced CAV and CYV can be reoxidized electrochemically at anodes of electrochemical cells. Anodes of silver, mercury or various forms of carbon are particularly suitable for this oxidation.

The reoxidation of reduced CAV or CYV is also possible with atmospheric oxygen. This is particularly surprising in the presence of whole cells or crude extracts of Proteus vulgaris, since the oxidoreductase which it contains is very sensitive to oxygen when it is used as reductase (S. Neumann, Thesis, Munich Technical University). The reduced CAV or CYV can also be reoxidized with electron acceptors, such as potassium hexacyanoferrate or other iron(III) compounds, and hydrogen peroxide.

The novel process is particularly useful for the oxidation of α-hydroxycarboxylic acids to the corresponding ketocarboxylic acids. In the presence of CAV or CYV, the 2-oxo acid reductase dehydrogenates only the R form of an α-hydroxycarboxylic acid. For example, the R-antipode in the mixture can be oxidized and the oxidation product (for example the corresponding ketoacid) can be removed from the mixture or, if required, subsequently converted to the desired compound by changing the applied voltage and exchanging the enzyme$. It is also possible selectively to dehydrogenate complex natural substances, such as meso-tartaric acid or gluconic acid.

With the aid of the novel process, it is also possible to oxidize NADH and NADPH to NAD+ and NADP+, respectively, and thus regenerate the latter for oxidation reactions. For example, the oxidation of NADH can be carried out using commercial lipoamide dehydrogenase from pig's liver and a methyl viologen-dependent pyridine nucleotide reductase from thermophilic Bacillus DSM 406. The last-mentioned pyridine nucleotide reductase can also be used to oxidize NADPH. To date, it has only been possible to use these enzymes to regenerate NADH or NADPH (J. Org. Chem. 46 (1981), 4100 and Angew. Chem. 97 (1985), 541).

The particular advantage of CAV and CYV is that they react with oxo acid reductases and that the equilibrium in the dehydrogenation reaction is advantageous. Hence, biochemical oxidation reactions can be carried out readily and rapidly with them.

EXAMPLE 1

30 ml of an anolyte (0.1M potassium phosphate, pH 8.5) of an electrochemical cell having a graphite electrode, e.g. Glassy Carbon (Sigraflex ® or Sigratex ®) as the anode contained 150 μmol each of R- and S-lactate, 2 mM of CAV++ and 10 mg (dry weight) of Proteus vulgaris. 47% of the total lactate were oxidized at a potential of −440 mV against a standard calomel electrode at pH 8.5 in the course of 7 h, according to the current curve. An enzymatic test showed that the mixture contained 130 μmol of pyruvate and 168 μmol of S-lactate.

The enzyme was deactivated by heat and the viologen-dependent NAD reductase from the thermophilic Bacillus DSM 406, 1.5 mM NAD and S-lactate dehydrogenase were added, after which the cell, operated at −640 mV in this case, was used to reduce the pyruvate. A total of 252 μmol of S-lactate was obtained. 15. The same result was obtained when the reaction was carried out with CYV at pH 7.0.

EXAMPLE 2

3.3 mmol of (R,S)-2-hydroxy-4-methylpentanoate were reacted with 1.5 mM of CAV++ and 32 mg of Proteus vulgaris at pH 8.5 in 55 ml of anolyte (0.1 M potassium phosphate, pH 8.5) of an electrochemical cell. After 5 h, current no longer flowed through the cell. HPLC analysis indicated the presence of 1.62 mmol of 2-oxo-4-methylpentanoate and 1.57 mmol of 2-hydroxy acid. Analysis over a Chiral-1 column from M & N, which gave good separation of R- and S-hydroxycarboxylic acid, indicated the presence of <2% of the R-enantiomer.

EXAMPLE 3

The following mixtures were shaken at 35° C. under air in Warburg vessels: 3.0 ml of tris . HCl buffer at Hp 8.5, 20 mg of P. vulgaris (dry weight), 2 mM CAV++ and 100 μmol of racemic mixtures of hydroxy acids. The reactions were complete after 4 h. The table below shows the results obtained.

TABLE

| Starting material | End Product |
| --- | --- |
| (R,S)-lactate | 58.0 μmol of S-lactate[x] |
| (Rs,S)-phenyllactate | 53.3 μmol of S-phenyllactate |
|  | 46.3 μmol of phenyl pyruvate |
| (R,S)-hydroxybutyrate | 50.2 μmol of S-hydroxybutyrate |
|  | 49.3 μmol of ketobutyrate |
| (R,S)-2-hydroxyglutarate | 58.0 μmol of S-hydroxyglutarate[x] |
| (R,S)-2-hydroxy-3-methyl-butanoate | 49.7 μmol of S-hydroxy compounds |
|  | 48.0 μmol of 2-keto-3-methyl-butyrate |

[x]The resulting keto acid is metabolized by the cells.

EXAMPLE 4

The following were incubated in 2.5 ml of 0.08M potassium phosphate buffer at pH 8.35: 40 mN (S)-Lactate, 2 mM CAV++, 0.95 mMNADH, 95 U of (S)-Lactate dehydrogenase of mammal origin and 2.5 U of viologen-dependent NAD(P)H oxidoreductase from Bacillus DSM 406. The mixture was shaken in an oxygen atmosphere at 35° C. After 22 h, about 90% of the expected pyruvate could be determined enzymatically. The activity of the Lactate dehydrogenase was 40% of the original value.

A similar experiment with (R)-Lactate and (R)-Lactate dehydrogenase from Lactobacillus leichmannii gave the same result. The remaining activity of the Lactate dehydrogenase was 60%. When the experiments were carried out in the presence of about 13,000 U of catalase, the results obtained were not significantly different.

We claim:

1. A process for carrying out enzymatic oxidations of alpha-hydroxycarboxylic acids to the corresponding ketocarboxylic acids, which process comprises transferring electrons from the alpha-hydroxycarboxylic acid to an electron acceptor in the presence of a redox enzyme wherein the electrons are transferred from the redox enzyme to the electron acceptor in the presence of a catalytic amount of CAV of CYV, thereby forming the ketocarboxylic acid corresponding to the alpha-hydroxycarboxylic acid.

* * * * *